United States Patent
Cole et al.

(10) Patent No.: US 9,254,280 B2
(45) Date of Patent: Feb. 9, 2016

(54) MEDICAL FOOD FOR COGNITIVE DECLINE

(75) Inventors: Gregory M. Cole, Santa Monica, CA (US); Sally A. Frautschy, Santa Monica, CA (US); David R. Schubert, La Jolla, CA (US); Pamela A. Maher, La Jolla, CA (US)

(73) Assignees: The Regents of the University of California, Oakland, CA (US); Salk Institute for Biological Studies, La Jolla, CA (US); U.S. Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/118,187

(22) PCT Filed: May 18, 2012

(86) PCT No.: PCT/US2012/038720
§ 371 (c)(1),
(2), (4) Date: Feb. 4, 2014

(87) PCT Pub. No.: WO2012/159092
PCT Pub. Date: Nov. 22, 2012

(65) Prior Publication Data
US 2014/0142172 A1    May 22, 2014

Related U.S. Application Data

(60) Provisional application No. 61/488,003, filed on May 19, 2011.

(51) Int. Cl.
| A61K 31/202 | (2006.01) |
| A61K 31/353 | (2006.01) |
| A61K 31/352 | (2006.01) |
| A23L 1/30 | (2006.01) |

(52) U.S. Cl.
CPC ............ *A61K 31/353* (2013.01); *A23L 1/3002* (2013.01); *A23L 1/3008* (2013.01); *A61K 31/202* (2013.01); *A61K 31/352* (2013.01); *A23V 2002/00* (2013.01)

(58) Field of Classification Search
CPC ........................... A61K 31/353; A61K 31/202
USPC .......................................................... 514/456
See application file for complete search history.

(56) References Cited

U.S. PATENT DOCUMENTS

2010/0021573 A1 * 1/2010 Gonzalez et al. ............. 424/766

FOREIGN PATENT DOCUMENTS

| EP | 0342795 A2 | 11/1989 |
| EP | 1419780 A1 | 5/2004 |
| JP | 2007-463794 A | 6/2007 |
| KR | 20090107607 A | 10/2009 |
| WO | 2010088700 A1 | 8/2010 |

OTHER PUBLICATIONS

Akaishi; et al., "Structural requirements for the flavonoid fisetin in inhibiting fibril formation of amyloid β protein," Neuroscience Letters (Oct. 31, 2008), 444(3):280-285.
Cole; et al., "DHA May Prevent Age-Related Dementia," J. Nutr. (Apr. 2010), 140(4):869-874.
Green; et al., "Dietary Docosahexaenoic Acid and Docosapentaenoic Acid Ameliorate Amyloid- and Tau Pathology via a Mechanism Involving Presenilin 1 Levels," J. Neurosci (Apr. 18, 2007), 27(16):4385-4395.
Maher, "A comparison of the neurotrophic activities of the flavonoid fisetin and some of its derivatives," Free Radic Res (Oct. 2006), 40(10):1105-11.
Maher et al., "Flavonoid fisetin promotes ERK-dependent long-term potentiation and enhances memory," PNAS (Oct. 31, 2006), 103(44):16568-73.
Maher, "The flavonoid fisetin promotes nerve cell survival from trophic factor withdrawal by enhancement of proteasome activity," Arch Biochem Biophys (Aug. 15, 2008), 476(2):139-44.
Maher, "Modulation of multiple pathways involved in the maintenance of neuronal function by fisetin," Micronutrients and Brain Health (2010), pp. 189-206.

* cited by examiner

*Primary Examiner* — Erich A Leeser
(74) *Attorney, Agent, or Firm* — Bozicevic, Field & Francis LLP; Pamela J. Sherwood

(57) ABSTRACT

Nutraceutical formulations that improve cognitive function in adults diagnosed with neurodegenerative disease are provided, which comprise a combination of fisetin and DHA.

16 Claims, 4 Drawing Sheets

MEDICAL FOOD FOR COGNITIVE DECLINE

PRIORITY

This application claims the benefit of priority to U.S. Provisional Application 61/488,003, filed May 19, 2011.

GOVERNMENT RIGHTS

This invention was made with Government support under AG035878, awarded by the National Institutes of Health (NIH). The Government has certain rights in the invention. This work was also supported by the U.S. Department of Veterans Affairs, and the Federal Government has certain rights in the invention.

BACKGROUND OF THE INVENTION

Alzheimer's disease (AD) is a degenerative disorder of the brain. It is the leading cause of dementia in elderly persons. AD patients have increased problems with memory loss and intellectual functions which progress to the point where they cannot function as normal individuals. With the loss of intellectual skills the patients exhibit personality changes, socially inappropriate actions and schizophrenia. AD is devastating for both victims and their families, for currently there is no effective palliative or preventive treatment for the inevitable neurodegeneration.

At a macroscopic level, the brains of AD patients are usually smaller, sometimes weighing less than 1,000 grams. At a microscopic level, the histopathological hallmarks of AD include neurofibrillary tangles (NFT), neuritic plaques, and degeneration of neurons. AD patients exhibit degeneration of nerve cells in the frontal and temporal cortex of the cerebral cortex, pyramidal neurons of the hippocampus, neurons in the medial, medial central, and cortical nuclei of the amygdala, noradrenergic neurons in the locus coeruleus, and the neurons in the basal forebrain cholinergic system. Loss of neurons in the cholinergic system leads to a consistent deficit in cholinergic presynaptic markers in AD.

The microtubule-associated protein known as Tau has been implicated in Alzheimers disease etiology. Tau binds to microtubules and assists with their formation and stabilization. However when tau is hyperphosphorylated, it is unable to bind and the microtubules become unstable and begin disintegrating. The unbound tau clumps together in formations called neurofibrillary tangles. More explicitly, intracellular lesions known as pretangles develop when tau is phosphorylated excessively and on improper amino acid residues. These lesions, over time, develop into filamentous neurofibrilary tangles (NFTs) which interfere with numerous intracellular functions.

Three different maturation states of NFT have been defined using anti-tau and anti-ubiquitin immunostaining. At stage 0 there are morphologically normal pyramidal cells showing diffuse or fine granular cytoplasmic staining with anti-tau. At stage 1 some delicate elongate inclusions are stained by tau antibodies; stage 2 is represented by the classic NFT demonstration with anti-tau staining; stage 3 is exemplified by ghost tangles where the host neuron has died, which are characterized by a reduced anti-tau but marked anti-ubiquitin immunostaining. It has been shown that the degree of cognitive impairment in diseases such as AD significantly correlates with the presence of neurofibrillary tangles.

The development of agents that can decrease cognitive decline, which may be a tauopathy, is of great interest for clinical and research purposes.

PUBLICATIONS

Cole and Frautschy, The Journal of Nutrition, first published as doi: 10.3945/jn.109.113910. Green et al. (2007) J. Neurosci. 27 (16) 4385-95; Maher (2010) In Micronutrients and Brain Health, L. Parker, H. Sies, M. Eggersdorfer, and E. Cardenas, eds. (Boca Raton, Fla., CRC Press), pp. 189-206, Genes Nutr. 2009 Sep. 10; Akaishi et al. (2008) Neurosci Lett. 444(3):280-5; Maher (2008) Arch Biochem Biophys. 476(2): 139-44; Maher et al. (2006) P.N.A.S. 103(44):16568-73; Maher (2006) Free Radic Res. 40(10):1105-11.

SUMMARY OF THE INVENTION

The present invention is based, at least in part, on the discovery of novel nutraceutical formulations that improve cognitive function in adults diagnosed with neurodegenerative disease. Diseases of interest include those associated with beta amyloid and tau/tangle pathology, which may include cognitive decline with aging or Alzheimer's disease, frontal temporal dementia, Pick's, and progressive supranuclear palsy. The compositions of the invention provide a combined dose of docosahexaenoic acid (DHA) and fisetin effective in slowing or treating cognitive decline.

The novel formulations include a combination of fisetin and DHA, which unexpectedly behaves synergistically. Accordingly, the formulations of the invention provide a novel therapeutic approach for improving cognition, for example in aging adults and in adults diagnosed with neurodegenerative disease. The invention features, in a first aspect, methods of improving cognitive performance in a subject, comprising administering to the subject a nutraceutical formulation or composition of the invention. In an exemplary embodiment, the subject has been diagnosed with Alzheimer's Disease.

Other features and advantages of the invention will be apparent from the following detailed description, and from the claims.

DEFINITIONS

Figure 1:
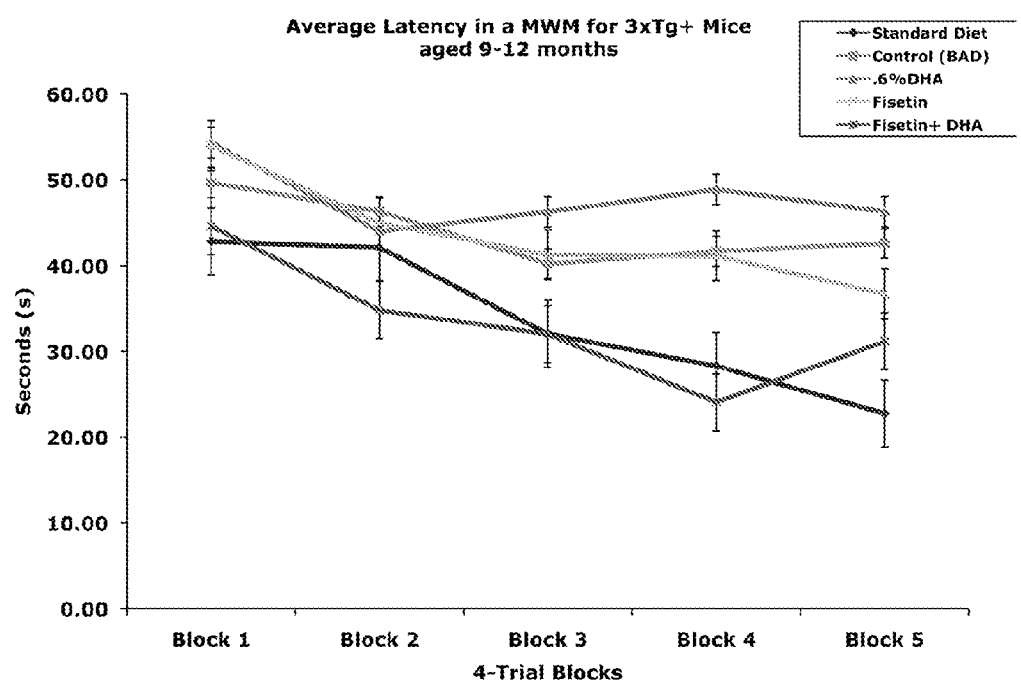
FIG. 1. Morris Water Maze results.

The compositions of the present invention can be formulated according to known methods to prepare pharmaceutically and nutraceutically useful compositions, whereby these materials, or their functional derivatives, are combined in admixture with a pharmaceutically or nutraceutically acceptable carrier vehicle. Suitable pharmaceutical vehicles and their formulation, inclusive of other human proteins, e.g., human serum albumin, are described, for example, in Remington's Pharmaceutical Sciences (16.sup.th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

An effective amount varies depending upon the health and physical condition of the subject to be treated, the taxonomic group of subjects to be treated (e.g. human, nonhuman primate, etc.), the capacity of the subject's nervous system, the degree of protection desired, the treating doctor's assessment of the medical situation, the condition to be treated or prevented, and other relevant factors.

Before the present compositions and methods are described in further detail, it is to be understood that this invention is not limited to particular methods described, as such may, of course, vary. It is also to be understood that unless stated otherwise, the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, subject to any specifically excluded limit in the stated range.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Fisetin (2-(3,4-dihydroxyphenyl)-3,7-dihydroxy-4H-chromen-4-one) is a yellow flavonoid polyphenol present at very low quantities in many foods, notably strawberries. Like resveratrol, it has been reported as a sirtuin-activating compound. Like many other polyphenols, it has pleiotropic antioxidant and anti-inflammatory activities (see, for example, Geraets et al. (2009) Biochemical and Biophysical Research Communications 382 (3): 598-603).

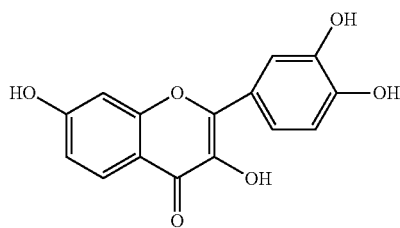 [SMILES: O=c1c(O)c(-c2ccc(O)c(O)c2)oc2cc(O)ccc12]

DHA (Docosahexaenoic acid; all-cis-docosa-4,7,10,13,16,19-hexa-enoic acid) is an omega-3 fatty acid that is a primary structural component of the human cerebral cortex, sperm, testicles and retina. It can be synthesized from alpha-linolenic acid or obtained directly from fish oil.

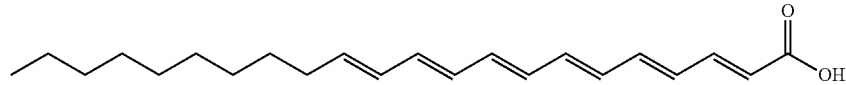 [SMILES: CCCCCCCCC/C=C/C=C/C=C/C=C/C=C/C=C/C(=O)O]

Cold-water oceanic fish oils are rich in DHA. Most of the DHA in fish and multi-cellular organisms with access to cold-water oceanic foods originates from photosynthetic and heterotrophic microalgae, and becomes increasingly concentrated in organisms the further they are up the food chain. DHA is also commercially manufactured from microalgae; *Crypthecodinium cohnii* and another of the genus *Schizochytrium*. In humans, DHA is either obtained from the diet or synthesized from eicosapentaenoic acid (EPA, 20:5, ω-3) via docosapentaenoic acid (DPA, 22:5 ω-3) as an intermediate.

DHA is the most abundant omega-3 fatty acid in the brain and retina. DHA comprises 40% of the polyunsaturated fatty acids in the brain and 60% of the PUFAs in the retina. Fifty percent of the weight of a neuron's plasma membrane is composed of DHA. DHA modulates the carrier-mediated transport of choline, glycine, and taurine, the function of delayed rectifier potassium channels, and the response of rhodopsin contained in the synaptic vesicles, among many other functions. DHA deficiency is associated with cognitive decline (see Lukiw et al. (2005) *J Clin Invest.* 115 (10): 2774-83).

Preliminary studies indicated that DHA can slow the progression of Alzhiemer's disease in mice. However, the first large-scale human trials showed that DHA alone did not slow decline of mental function in elderly people with mild to moderate Alzheimer's disease (Quinn et al. (2010) JAMA 304 (17): 1903-11). These trials were part of a large U.S. National Institutes of Health (NIH) intervention study to evaluate DHA in Alzheimer's disease.

Detailed Description Of The Embodiments

The present invention is based, at least in part, on the discovery of novel nutraceutical formulations which improve cognitive function, e.g. in adults diagnosed with neurodegenerative disease, such as early-stage and mid/late-stage Alzheimer's Disease. The development of non-prescription nutraceutical formulations is highly desirable as both a preventative measure, as well as to augment any pharmacological treatment approaches. Such nutraceutical formulations also are useful for normal subjects, e.g., normal adults seeking to improve cognitive function.

The nutraceutical formulations described herein contain components that synergistically provide neuroprotection against undesirable inflammation and development of filamentous neurofibrilary tangles (NFTs) which interfere with numerous intracellular functions. Co-administration of the components of the nutraceutical formulations maintained and/or improved cognitive performance over an extended period of time in the animal model 3xAD transgenic mice, indicating that the combination of components is useful in treating and/or reducing the symptoms associated with AD and other taouopathies.

The formulations can be used or administered alone, or together in combination with other nutraceutical or pharmaceutical compositions. Nutraceutical or pharmaceutical compositions suitable for administration in combination with the formulations of the invention include nutraceutical or pharmaceutical compositions effective in improving cognition or reducing symptoms associated with a neurological disorder (e.g., Alzheimer's disease and other taouopathies). The compositions of the invention may be administered to a mammal, e.g. a mouse, including mouse models for neurologic disease, a human, etc.

In some preferred embodiments, the formulation is administered orally. In an alternative embodiment, the formulation is administered parenterally. In a further embodiment of these aspects, the formulation is administered as a unit dosage form. A combination product of the invention can be defined based on the weights of the two agents per dosage unit. On a weight basis, the ratio of fisetin to DHA is usually from about 20:1 to about 1:20; from about 10:1 to about 1:10; from about 5:1 to about 1:5; from about 2:1 to about 1:2; and in some embodiments is about 1:6, about 1:10, about 1:15 or about 1:20.

In an exemplary embodiment, the unit dose of the formulation comprises DHA in an amount of at least about 25 mg, at least about 100 mg, at least about 500 mg, at least about 1 g, at least 2 g, at least about 5 g, or at least about 10 g. The unit dose of the formulation may comprise fisetin in an amount of at least about 10 mg, at least about 50 mg, at least about 100 mg, at least about 250 mg, at least about 500 mg, at least about 1 g, at least about 2 g, at least about 5 g, or at least about 10 g. Nutraceutical formulations can be prepared using methods known in the art. Optionally the nutraceutical formulation further comprises one or more anti-oxidants in addition to the fisetin and DHA, e.g. ascorbic acid, coenzyme Q, etc.

In an exemplary embodiment, the unit dose of the formulation comprises DHA in an amount of at least about 25 mg, at least about 100 mg, at least about 500 mg, at least about 1 g, at least 2 g, at least about 5 g, or at least about 10 g. The unit dose of the formulation may comprise fisetin in an amount of at least about 10 mg, at least about 50 mg, at least about 100 mg, at least about 250 mg, at least about 500 mg, at least about 1 g, at least about 2 g, at least about 5 g, or at least about 10 g. Nutraceutical formulations can be prepared using methods known in the art. Additional information regarding nutraceuticals can be found at the Natural Products Association.

Table 1 sets forth certain preferred embodiments of the instant nutraceutical composition with respect to the amounts of DHA and fisetin present in the composition. Such composition, which preferably is for human oral consumption, is envisioned for daily consumption to treat an existing cognitive disorder (e.g., AD) or improve cognition in a "normal" subject (i.e., a subject who has an as yet undiagnosed cognitive disorder or a subject (preferably over the age of 60) who has no cognitive disorder). Additional delivery regimens for these compositions include twice per day, once every two days, once every three days, and once per week.

TABLE 1

| Composition # | Fisetin (mg) | DHA (mg) |
|---|---|---|
| 1 | 100 | 100 |
| 2 | 100 | 150 |
| 3 | 100 | 200 |
| 4 | 100 | 250 |
| 5 | 100 | 300 |
| 6 | 100 | 350 |
| 7 | 100 | 400 |
| 8 | 100 | 450 |
| 9 | 100 | 500 |
| 10 | 100 | 550 |
| 11 | 100 | 600 |
| 12 | 100 | 650 |
| 13 | 100 | 700 |
| 14 | 100 | 750 |
| 15 | 100 | 800 |
| 16 | 100 | 850 |
| 17 | 100 | 900 |
| 18 | 100 | 950 |
| 19 | 100 | 1000 |
| 20 | 150 | 100 |
| 21 | 150 | 150 |
| 22 | 150 | 200 |
| 23 | 150 | 250 |
| 24 | 150 | 300 |
| 25 | 150 | 350 |
| 26 | 150 | 400 |
| 27 | 150 | 450 |
| 28 | 150 | 500 |
| 29 | 150 | 550 |
| 30 | 150 | 600 |
| 31 | 150 | 650 |
| 32 | 150 | 700 |
| 33 | 150 | 750 |
| 34 | 150 | 800 |
| 35 | 150 | 850 |
| 36 | 150 | 900 |
| 37 | 150 | 950 |
| 38 | 150 | 1000 |
| 39 | 175 | 100 |
| 40 | 175 | 150 |
| 41 | 175 | 200 |
| 42 | 175 | 250 |
| 43 | 175 | 300 |
| 44 | 175 | 350 |
| 45 | 175 | 400 |
| 46 | 175 | 450 |
| 47 | 175 | 500 |
| 48 | 175 | 550 |
| 49 | 175 | 600 |
| 50 | 175 | 650 |
| 51 | 175 | 700 |
| 52 | 175 | 750 |
| 53 | 175 | 800 |
| 54 | 175 | 850 |
| 55 | 175 | 900 |
| 56 | 175 | 950 |
| 57 | 175 | 1000 |
| 58 | 200 | 100 |
| 59 | 200 | 150 |
| 60 | 200 | 200 |
| 61 | 200 | 250 |
| 62 | 200 | 300 |
| 63 | 200 | 350 |
| 64 | 200 | 400 |
| 65 | 200 | 450 |
| 66 | 200 | 500 |
| 67 | 200 | 550 |
| 68 | 200 | 600 |
| 69 | 200 | 650 |
| 70 | 200 | 700 |
| 71 | 200 | 750 |
| 72 | 200 | 800 |
| 73 | 200 | 850 |
| 74 | 200 | 900 |
| 75 | 200 | 950 |
| 76 | 200 | 1000 |
| 77 | 250 | 100 |
| 78 | 250 | 150 |
| 79 | 250 | 200 |
| 80 | 250 | 250 |
| 81 | 250 | 300 |
| 82 | 250 | 350 |
| 83 | 250 | 400 |
| 84 | 250 | 450 |
| 85 | 250 | 500 |
| 86 | 250 | 550 |
| 87 | 250 | 600 |
| 88 | 250 | 650 |
| 89 | 250 | 700 |
| 90 | 250 | 750 |
| 91 | 250 | 800 |
| 92 | 250 | 850 |
| 93 | 250 | 900 |
| 94 | 250 | 950 |
| 95 | 250 | 1000 |
| 96 | 300 | 100 |
| 97 | 300 | 150 |
| 98 | 300 | 200 |
| 99 | 300 | 250 |
| 100 | 300 | 300 |
| 101 | 300 | 350 |
| 102 | 300 | 400 |
| 103 | 300 | 450 |
| 104 | 300 | 500 |
| 105 | 300 | 550 |

TABLE 1-continued

| Composition # | Fisetin (mg) | DHA (mg) |
|---|---|---|
| 106 | 300 | 600 |
| 107 | 300 | 650 |
| 108 | 300 | 700 |
| 109 | 300 | 750 |
| 110 | 300 | 800 |
| 111 | 300 | 850 |
| 112 | 300 | 900 |
| 113 | 300 | 950 |
| 114 | 300 | 1000 |

The nutraceutical formulations for use in accordance with the present invention can be formulated in a conventional manner using one or more physiologically acceptable carriers or excipients. Agents used in the formulations and their physiologically acceptable salts and solvates can be prepared for administration by various methods. In an exemplary embodiment, administration of the formulations is oral (ideally solid or liquid). In an alternative embodiment, administration is parenteral, e.g., intravenous, subcutaneous, intramuscular, intracranial, intraorbital, ophthalmic, intraventricular, intracapsular, intraspinal, intracisternal, intraperitoneal, or transmucosal. The compositions can be formulated in various ways, according to the route of administration.

For oral administration, the formulations can take the form of, for example, tablets or capsules, prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice, e.g., apple juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). Other suitable non-aqueous vehicles may include neuroprotective foods, e.g., fish oil, flax seed oil, etc. The preparations can also contain buffer salts, flavoring, coloring and sweetening agents as appropriate.

Preparations for oral administration may be provided as a unit dosage form, for example, as tablets, capsules, etc. These can be presented in blister packs or in multi-dose containers. Preparations for oral administration can also be suitably formulated to give controlled release of the active compound.

For buccal or sublingual administration the formulations can take the form of tablets or lozenges formulated in conventional manner. The formulations can be prepared for parenteral administration by injection, for example, by bolus injection or continuous infusion. Formulations for injection can be presented in unit dosage form, for example, in ampoules or in multi-dose containers, with an added preservative. The formulations can take such forms as suspensions, solutions or emulsions in oily or aqueous vehicles, and can contain formulatory agents such as suspending, stabilizing and/or dispersing agents. Alternatively, the active ingredients can be in powder form for constitution with a suitable vehicle, for example, sterile pyrogen-free water, before use.

The formulations can also be prepared in rectal compositions such as suppositories or retention enemas, for example, containing conventional suppository bases such as cocoa butter or other glycerides.

The formulations can also be provided as a depot preparation. Such long acting formulations may be administered by implantation (for example subcutaneously or intramuscularly) or by intramuscular injection. Thus, for example, the formulations can be prepared with suitable polymeric or hydrophobic materials (for example as an emulsion in an acceptable oil) or ion exchange resins, or as sparingly soluble derivatives, for example, as a sparingly soluble salt.

The formulations can be presented in a pack or dispenser device, which may contain one or more unit dosage forms containing the active ingredient. The pack may, for example, comprise metal or plastic foil, such as a blister pack. The pack or dispenser device can be accompanied by instructions for administration.

The therapeutic formulations of the invention can also contain a carrier or excipient, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol.

Methods useful for making formulations are known in the art and can be found in, for example, Remington's Pharmaceutical Sciences (Gennaro, ed., Williams & Wilkins, Baltimore, Md.).

The invention additionally features methods of treating a neurodegenerative disorder in a subject, involving administering a therapeutically effective amount of a composition of the invention to the subject, such that the disorder is treated. The invention further features methods of reducing symptoms associated with a neurodegenerative disorder in a subject, involving administering a therapeutically effective amount of a composition of the invention to the subject, such that the symptoms of the disorder are reduced.

In general, the instant composition may act, for example, by (i) eliminating a cognitive disorder, (ii) ameliorating one or more symptoms of a cognitive disorder, (iii) slowing the progression of a cognitive disorder, (iv) delaying the onset of a cognitive disorder's symptoms, and (v) reducing the likelihood of a cognitive disorder's onset.

Importantly, the combination of components of the formulations has been discovered to be more effective than the individual components in the uses of the invention. As the results described herein indicate, the degree of efficacy of the particular formulations of the invention was completely unanticipated, indicating that these unique combinations synergistically provide neuroprotection. Although convenient for administration, it is not necessary for the agents or components of the nutraceutical formulations to be compounded together for administration to a subject. Instead, they can be administered concurrently, or in close enough succession so that the desired dosage level for all components is achieved in the bloodstream at the same time.

In general, a nutraceutical formulation is formulated by combining appropriate concentrations of stock agent (e.g., in solution or solid) of the components in a medium. The components can be administered together, in rapid succession, or at intervals. A composition may be tested to determine whether it is an effective nutraceutical formulation in an in vitro cell culture system of primary, secondary, or immortalized neural cells, for example, cells that exhibit the molecular and biochemical characteristics of normal neural cells, or cells that exhibit at least some of the molecular and biochemical characteristics of a neurologic disorder. Such cells and methods of evaluating the effects of the formulations are known in the art, and exemplary cells and methods are described in the Examples. Biochemical and physical criteria can be used to measure the ability of a nutraceutical formulation to ameliorate adverse events associated with aging and inflammation. Biochemical and physical criteria can additionally be used to measure the ability of a nutraceutical formulation to ameliorate adverse effects associated with a disorder in these cell culture systems.

Animal models are likewise useful for evaluating the efficacy of a nutraceutical formulation. Nutraceutical formulations can be evaluated in vivo using an animal model, for example, an animal model for AD. Examples of animal models for AD are mice expressing the human E4 allele of ApoE, mice expressing the human form of the protein Tau, and other transgenic mouse lines in which expression of the amyloid precursor protein (APP) gene is affected (Reaume et al., J. Biol. Chem., 271:23380-23388, 1996; Hsiao et al., Science, 276:99-102, 1996; and Games et al., Nature, 373:523-527, 1995). Nutraceutical formulations can also be evaluated for their efficacy in preventing or ameliorating the effects of AD using an animal model. The effects of a nutraceutical formulation on ameliorating behavioral and biochemical symptoms in such mice are evaluated after administering a nutraceutical formulation to these mice both early in life and after symptoms begin to develop. Mice are evaluated for the development or progression of learning and memory disorders as well as for pathophysiologic and biochemical abnormalities such as the presence of plaques in cortical and limbic structures of the brain. Prevention of the onset or progression of symptoms, or the amelioration of existing symptoms, indicates that the nutraceutical formulation is effective for treating Alzheimer disease in humans.

While is not necessary for all of the components of a nutraceutical formulation to be administered in the same excipient, in the same form, or delivered at precisely the same time during a day, the components should be administered so they are present in the treated subject at the same time (e.g., present in a cell that is the target of treatment), and thus, one formulation, including both components, is generally provided in a convenient dosage form.

The nutraceutical formulations of the invention may be components in kits. These kits can also include instructions for administration of the formulations to a subject, and optionally may include one or more other nutraceuticals, e.g., ginko biloba, fish oil, apple juice, flax seed oil, and other nutraceutical foods or formulations known in the art. These kits may additionally include instructions for administration, and/or other nutraceutical foods or formulations.

This invention is further illustrated by the following examples, which should not be construed as limiting. The contents of all references, patents and published patent applications cited throughout this application are incorporated herein by reference.

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

EXAMPLES

The fish oil enriched omega 3 fatty acid DHA has been reported to be ineffective in treating mild to moderate Alzheimer disease patients who have extensive beta amyloid plaques and tangles. It has been shown that DHA can reduce the accumulation of beta amyloid but DHA appears to lose efficacy over time as pathology develops in an animal model with both beta amyloid and tangles (tau pathology), the 3×AD transgenic mouse. We found that fish oil alone was insufficient to treat the 3×AD Tg mouse.

Fisetin, a natural flavonoid enriched in strawberries, is neuroprotective and can improve cognitive function in various animal models including aging mice and beta amyloid plaque accumulating transgenic mice. We have tested 0.6% DHA alone, 500 ppm fisetin alone and DHA+fisetin in combination delivered as a food supplement (in chow) to older 3×AD Tg mice with combined amyloid and tau pathology. The study ran from ~9 months to 13-14 months of age. Cognitive deficits were improved by DHA+fisetin but not by DHA alone or fisetin alone (FIG. 1).

As shown in FIG. 1, Morris Water Maze results show no improvement in time (latency) to find a hidden platform with additional blocks of training when 12-13 month old 3×AD Tg mice are tested on control bad (high safflower oil) diet with or without DHA (green) or fisetin (light blue) but marked improvement over time with DHA+fisetin together.

Figure 2:
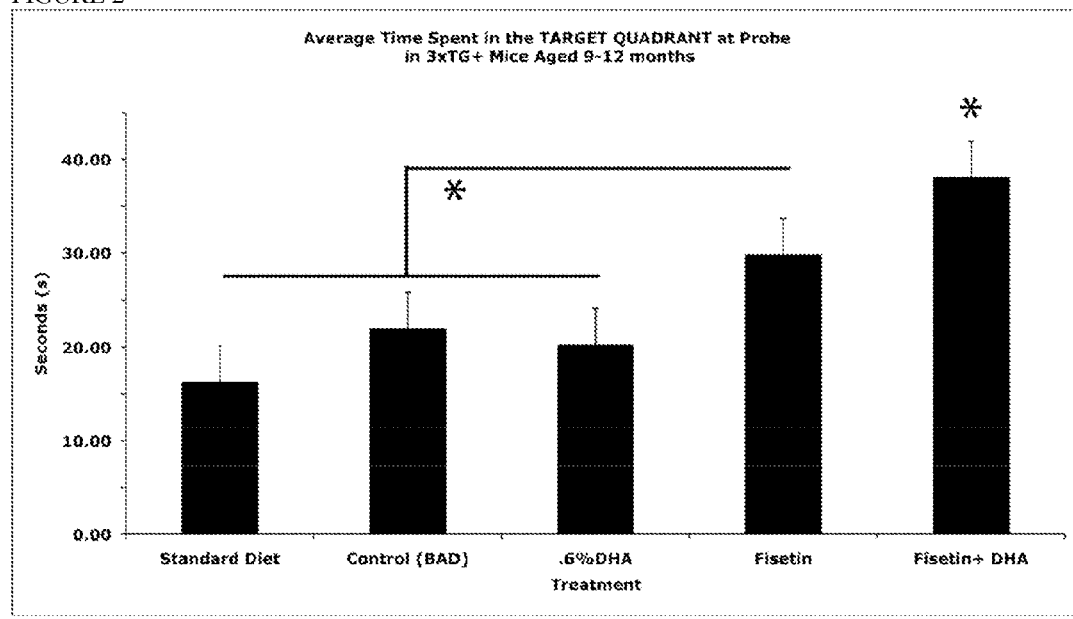
FIG. 2. Retention in the probe test.

FIG. 2. Shows that the dietary combination of fisetin and DHA improved retention in the probe test. In this test the platform is removed, and the mice are allowed to swim for 60 seconds, while the time in the target quadrant is quantified. Fisetin alone also improved retention, but the combination resulted in the best performance on this test.

Figure 3:
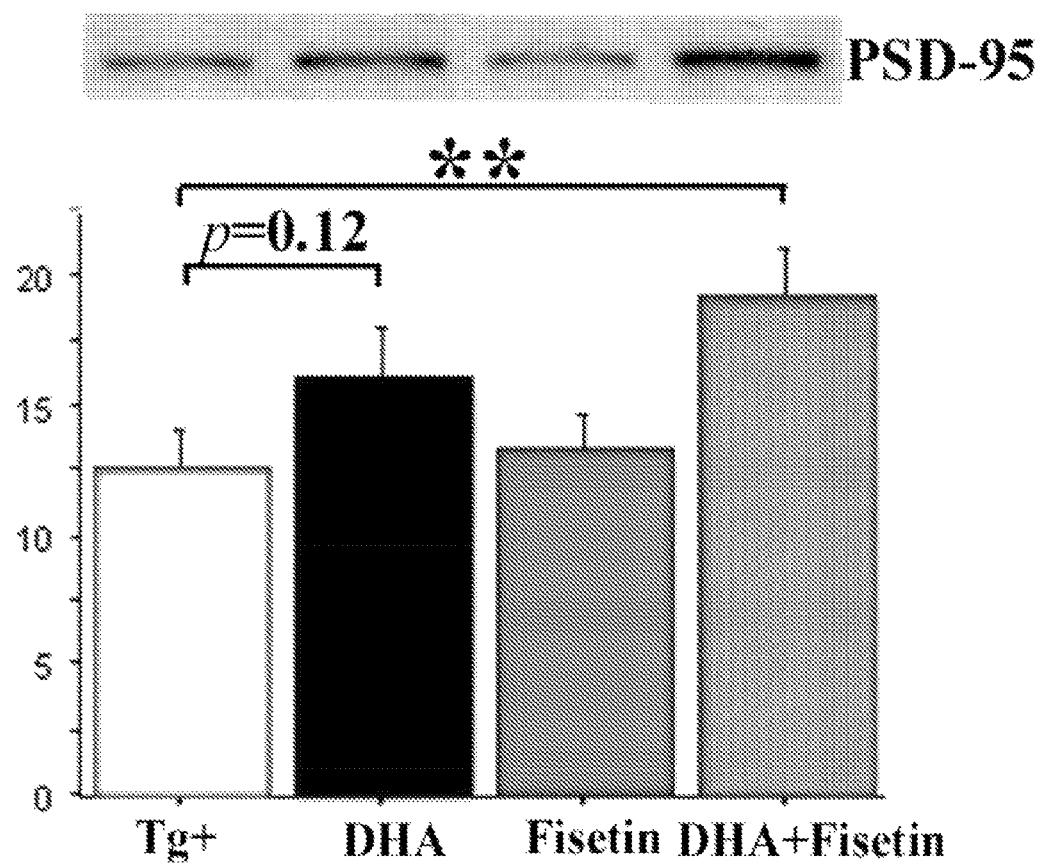
FIG. 3. Western analysis of proteins.
Figure 4:
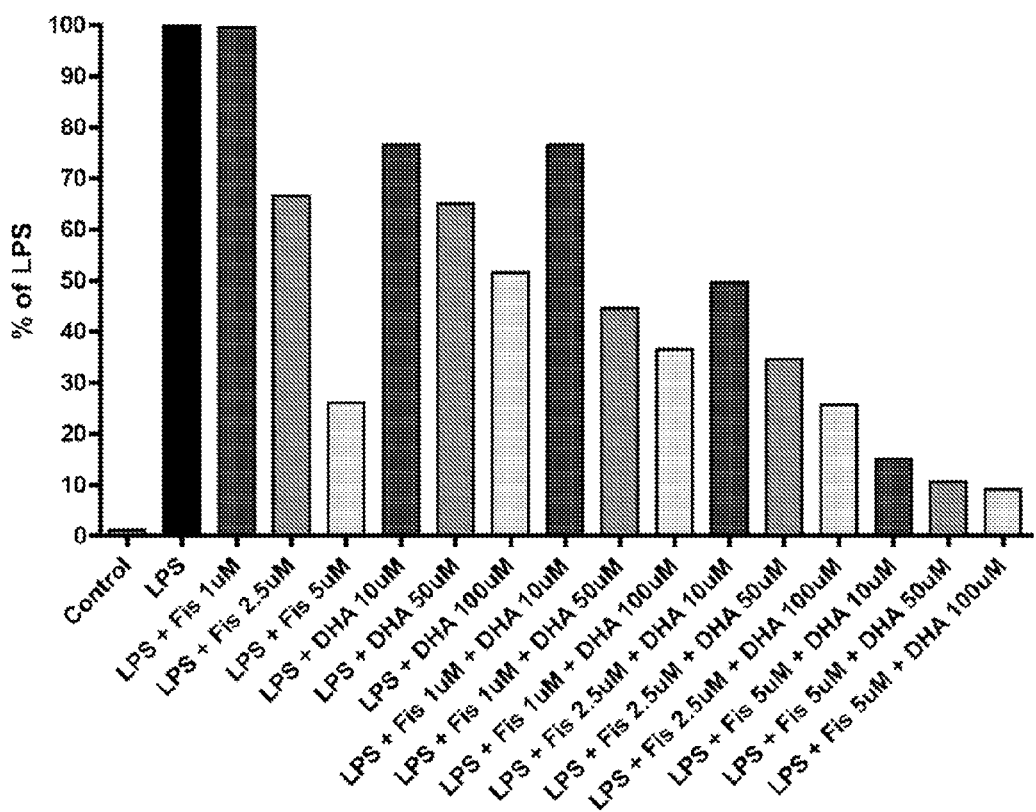
FIG. 4. Fisetin and DHA in N9 microglia cells.

FIG. 3. Western analysis of proteins from brain of the same 3×AD triple mice studied on the same diets as in FIG. 1 behavior studies. The excitatory synaptic marker PSD-95 is partially protected (increased) by DHA alone (trend) but not by fisetin but significantly protected by DHA+fisetin ($p<0.001$).

These data demonstrate that a treatment combining DHA and fisetin or fish oil and fisetin is a synergistic treatment for cognitive deficits. Since beta amyloid and tau/tangle pathology occur in normal aging and many years prior to Alzheimer diagnosis, DHA and fisetin can be effective in slowing cognitive decline with aging or Alzheimer's, or an effective treatment for these or other conditions with beta amyloid and or tauopathy related cognitive deficits including frontal temporal dementia, Pick's, progressive supranuclear palsy.

To demonstrate the synergistic activity of the two agents and to establish an appropriate fixed-dose ratio for clinical investigation, varying amounts of fisetin and DHA have been added to N9 microglia cells under simulated inflammatory conditions (i.e., 10 μg/ml LPS). After 24 hr NO release was measured in the culture medium as $NO_2$ using the Griess assay. Results are presented as the % of $NO_2$ in the culture medium of cells treated with LPS alone The combination of the two agents was found to have a strong synergistic effect on inflammation, particularly at the indicated enzyme ratios.

These data show that a combination of DHA and fisetin provide a synergistic improvement in anti-inflammatory activity. Effective ratios include without limitation those where fisetin is provided at a concentration of at least 5 µM, and where the ratio of DHA to fisetin may be at least about 1:2, 1:5, 1:10 or more.

What is claimed is:

1. A composition comprising a synergistic combined amount of fisetin and docosahexaenoic acid (DHA) in a ratio effective in reducing cognitive defects.

2. The composition of claim 1, wherein the ratio of fisetin to DHA by weight is from about 1:20 to 20:1.

3. The composition of claim 2, wherein the ratio of fisetin to DHA by weight is from about 1:1 to 1:20.

4. The composition of claim 3, wherein the ratio of fisetin to DHA by weight is from about 1:5 to 1:20.

5. The composition of claim 4, wherein the composition comprises at least 500 mg DHA.

6. A unit dose composition comprising a synergistic combined amount of fisetin and docosahexaenoic acid (DHA) effective in reducing cognitive defects, in a dose comprising at least about 1 g. DHA; and wherein the ratio of DHA to fisetin by weight is from about 1:2 to 1:10.

7. The composition of claim 6, wherein the composition comprises at least about 5 g. DHA.

8. The composition of claim 1, wherein the composition consists essentially of fisetin and DHA.

9. The composition of claim 1, wherein the composition is a dietary supplement.

10. The composition of claim 1, wherein the composition is formulated for administration to a subject.

11. The composition of claim 1, wherein the composition is formulated for use as a food additive.

12. The composition of claim 1, wherein the composition is formulated as a liquid.

13. A method of improving cognitive performance in a subject, the method comprising administering a composition according to claim 6.

14. The method of claim 13, wherein the subject suffers from a neurodegenerative disorder.

15. The method of claim 14, wherein the neurodegenerative disorder is Alzheimer's disease.

16. The method of claim 13, wherein the formulation is administered orally.

* * * * *